(12) United States Patent
Ye et al.

(10) Patent No.: US 7,750,148 B2
(45) Date of Patent: Jul. 6, 2010

(54) INTERMEDIATE COMPOUND FOR THE PRODUCTION OF β-LACTAMASE-RESISTANT CEPHALOSPORIN ESTER COMPOUNDS AND SALTS THEREOF

(75) Inventors: Fengqi Ye, Taizhou (CN); Shanzong Fang, Taizhou (CN); Xiuwei Lu, Taizhou (CN)

(73) Assignee: Zhejiang Yongning Pharmaceutical Factory, Zhejiang Province (CN)

( * ) Notice: Subject to any disclaimer, the term of this patent is extended or adjusted under 35 U.S.C. 154(b) by 418 days.

(21) Appl. No.: 10/580,561

(22) PCT Filed: Nov. 19, 2004

(86) PCT No.: PCT/CN2004/001318

§ 371 (c)(1),
(2), (4) Date: May 26, 2006

(87) PCT Pub. No.: WO2005/051959

PCT Pub. Date: Jun. 9, 2005

(65) Prior Publication Data

US 2007/0093464 A1    Apr. 26, 2007

(30) Foreign Application Priority Data

Nov. 28, 2003  (CN) .................... 2003 1 0108979
Sep. 29, 2004  (CN) .................... 2004 1 0083434

(51) Int. Cl.
C07D 501/22    (2006.01)
C07D 519/06    (2006.01)
A61K 31/546    (2006.01)
A61P 31/04     (2006.01)

(52) U.S. Cl. ..................... 540/223; 540/230
(58) Field of Classification Search ................ 540/223; 514/202, 207
See application file for complete search history.

(56) References Cited

U.S. PATENT DOCUMENTS 6,150,350 A * 11/2000 Angehrn et al. ............. 514/202

FOREIGN PATENT DOCUMENTS

GB    2113681 A    *    8/1983

OTHER PUBLICATIONS

Baltzer, The Journal of Antibiotics vol. 33 , No. 10(1980)pp. 1183-1192.*
Okonogi, The Journal of Antibiotics vol. 35 , No. 8(1982)pp. 963-971.*
Crosby, Antimicrob Agents Chemother. Sep. 1982; 22(3): 398-405.*
Bauernfeind, International Journal of Antimicrobial Agents vol. 6, Supplement 1, Apr. 1996, pp. S15-S26.*
Aubert, Journal of Antimicrobial Chemotherapy (1996) 37, 155-160.*
Xiong et al., Journal of Antimicrobial Chemotherapy (1995) 35, 697-706.*
Fu, Journal of Antimicrobial Chemotherapy (1984) 13, 257-265.*
Xiong, International Journal of Antimicrobial Agents (Mar. 2004), 23(3), 262-267.*
English, J Med Chem. Jan. 1990;33(1):344-7.*

* cited by examiner

*Primary Examiner*—Mark L Berch
(74) *Attorney, Agent, or Firm*—Rabin & Berdo, P.C.

(57) ABSTRACT

An intermediate compound represented by formula (IV) as follows:

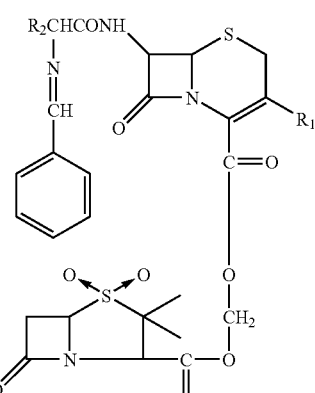

wherein, $R_1$= $CH_3$ or Cl;

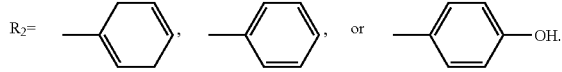

1 Claim, No Drawings

INTERMEDIATE COMPOUND FOR THE PRODUCTION OF β-LACTAMASE-RESISTANT CEPHALOSPORIN ESTER COMPOUNDS AND SALTS THEREOF

FIELD OF THE INVENTION

This invention relates to a series of β-lactamase resistant cephalosporin ester compounds and salts of thereof, as well as their use for preparation of the antibiotics.

BACKGROUND OF THE INVENTION

The compounds possessing the following formula (II) are all known semi-synthetic cephalosporin,

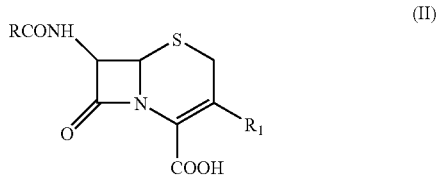

such as: cefetamet (CAS registration number 65052-63-3); cefuroxime (CAS registration number 55268-75-2); cefradine (CAS registration number 38821-53-3); cefalexin (CAS registration number 15686-71-2); cefaclor (CAS registration number 53994-73-3); and cefadroxil (registration number 50370-12-2). Among them, pivaloyloxymethyl ester of cefetamet (cefetamet pivoxil, CAS registration number 65243-33-6) and 1-(acetoxyl)ethyl ester of cefuroxime (cefuroxime axetil, CAS registration number 64544-07-6) along with another above-mentioned four kinds of cephalosporin are oral antibiotics which have been used in clinic.

The compound possessing the following formula (III) is:

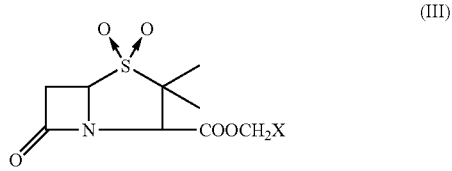

Sulbactam (CAS registration number 68373-14-8) halogen methyl ester, which belongs to β-lactamase inhibitor, with strong irreversible inhibition to β-lactamase released by *staphylococcus aureus* and many other Gram negative bacteria. It manifests extremely strong inhibition to type II, III, IV, V β-lactamase at a concentration of 2 μg/ml. If used with penicillin and cephalosporin antibiotics, it can generate synergetic effects; currently, mixed injections of ampicillin, cefoperazone, cefotaxim, ceftriaxone and sulbactam sodium salt have been used in clinic, which can prevent these antibiotics from losing antibacterial activities due to being hydrolyzed by β-lactamase, reducing minimum inhibitory concentration of these antibiotics to certain drug resistant bacteria resulting from lactamase production.

It is well known that intravenous administration is time-consuming, and has the potential threats of blood-borne infectious disease such as hepatitis B, C, AIDS etc. For those mild, moderate inflammation patients or sequential therapy of patients after intravenous anti-inflammation therapy, it is usually sufficient of oral administration, which is not only convenient and safe, but also can save a lot of manpower, material resources and wealth. However, drug resistance is quite common among oral β-lactam antibiotics to lactamase-producing bacteria, thus resulting in poor therapeutic reactions. Therefore, preparation of oral β-lactamase resistant antibiotics is actually a focus topic in the field of antibiotics manufacture.

At present, bis-esters sultamicillin (CAS registration number 76497-13-7), which is synthesized chemically by the compounds (III) and ampicillin, is an oral antimicrobial being widely used in clinic; it can be hydrolyzed to ampicillin and sulbactam by esterase of intestine walls, thus exerting the same therapeutic effects as the mixed injection of sulbactam and ampicillin. However, there is yet no compound which can chemically synthesize the compounds (III) and cephalosporin and further prepare oral β-lactamase resistant antibiotics.

SUMMARY OF THE INVENTION

The purpose of the present invention is to resolve the above topic, and to provide a β-lactamase resistant cephalosporin ester compound and salts of thereof.

The purpose of the present invention is accomplished by the following technical solution:

A β-lactamase resistant cephalosporin ester compound, the characterized in that the structures of the compound are composed by connecting methyl ester residue of sulbactam halomethyl ester with carboxyl residue of semi-synthetic cephalosporin or salts of thereof.

Wherein, salt of the semi-synthetic cephalosporin is inorganic salt or organic alkali salt.

The inorganic salt can be sodium salt, potassium salt, magnesium salt or calcium salt; the organic alkali salt can be triethylamine salt, tributylamine salt, 1,8-diazacyclo[5,4,0]undecane-7-ene salt, dicyclohexyl amine salt or tetrabutylammonium salt.

The semi-synthetic cephalosporin is selected from the group consisting of cefetamet, cefuroxime, cefradine, cefalexin, cefaclor or cefadroxil.

However, this sulbactam halomethyl ester can be sulbactam bromomethyl ester or sulbactam iodomethyl ester.

This invention also provides pharmaceutical salts of the above compound.

Wherein, this pharmaceutical salt is inorganic salt or organic acid salt.

This inorganic salt or organic acid salt can be hydrochloride, sulphate, p-toluenesulfonate, tartrate, maleate and lactate.

The compound or pharmaceutical salts thereof according to the invention, characterized in that the compound is represented by the following formula (I):

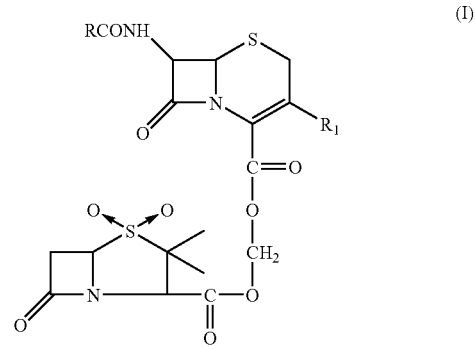

Wherein, the detailed meanings of R and $R_1$ are shown in the following table:

| Compound (I) code | Serial number | Common name | Compound (II) R | R₁ |
|---|---|---|---|---|
| YR-1 | II-1 | cefetamet | 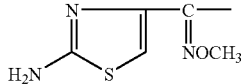 | —CH₃ |
| YR-2 | II-2 | cefuroxime | 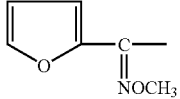 | —CH₂OCNH₂ (O) |
| YR-3 | II-3 | cefradine | 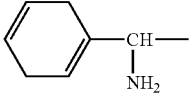 | —CH₃ |
| YR-4 | II-4 | cefalexin | 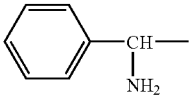 | —CH₃ |
| YR-5 | II-5 | cefadroxil | 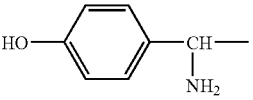 | —CH₃ |
| YR-6 | II-6 | cefaclor | 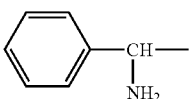 | —Cl |

Respective chemical names of this series of compounds (I) are listed as follows:

YR-1: 5-thia-1-aza-bicyclo [4,2,0] octane-2-ene-2-carboxylic acid, 7-[[(2-amino-4-thiazolyl) (methoxy imine) acetyl] amino]-3-methyl-8-oxo-, [[3,3-dimethyl-4,4-dioxy-7-oxo-4-thia-1-aza-bicyclo [3,2,0] heptane-2-group]carbonyloxy]oxy]methyl ester and salt thereof.

YR-2: 5-thia-1-aza-bicyclo [4,2,0] octane-2-ene-2-carboxylic acid, 7-[[(2-furane (methoxy imine) acetyl)amino]-3-[[(amino carbonyloxy)oxy]methyl]-8-oxo-, [[3,3-dimethyl-4,4-dioxy-7-oxo-4-thia-1-aza-bicyclo[3,2,0] heptane-2-group]carbonyloxy]oxy]methyl ester and salt thereof.

YR-3: 5-thia-1-aza-bicyclo [4,2,0] octane-2-ene-2-carboxylic acid, 7-[[amino-1,4-cyclohexadiene-1-group-acetyl] amino], 3-methyl-8-oxo-, [[3,3-dimethyl-4,4-dioxy-7-oxo-4-thia-1-aza-bicyclo [3,2,0] heptane-2-group] carbonyloxy]oxy]methyl ester and salt thereof.

YR-4: 5-thia-1-aza-bicyclo [4,2,0] octane-2-ene-2-carboxylic acid, 7-[[amino phenylacetyl]amino], 3-methyl-8-oxo-, [[3,3-dimethyl-4,4-dioxy-7-oxo-4-thia-1-aza-bicyclo [3,2,0] heptane-2-group]carbonyloxy]oxy]methyl ester and salt thereof.

YR-5: 5-thia-1-aza-bicyclo [4,2,0] octane-2-ene-2-carboxylic acid, 7-[[amino (4-hydroxyphenyl)-acetyl]amino]-8-oxo-, [[3,3-dimethyl-4,4-dioxy-7-oxo-4-thia-1-aza-bicyclo[3,2,0] heptane-2-group]carbonyloxy]oxy]methyl ester and salt thereof.

YR-6: 5-thia-1-aza-bicyclo [4,2,0] octane-2-ene-2-carboxylic acid, 7-[[amino phenylacetyl]amino], 3-cl-8-oxo-, [[3, 3-dimethyl-4,4-dioxy-7-oxo-4-thia-1-aza-bicyclo [3,2,0] heptane-2-group]carbonyloxy]oxy]methyl ester and salt thereof.

The compounds and salts thereof according to the invention have the same intravital metabolic characteristic as that of sultamicillin; they can be hydrolyzed to cephalosporin and sulbactam by esterase of intestine walls after being administered orally, and the intravital synergistic effect can compensate the disadvantage of these cephalosporins being hydrolyzed by β-lactamase which is released by certain bacteria, thus reducing minimum inhibitory concentration to those certain drug resistant bacteria resulting from lactamase production to the sensitive range.

They can be synthesized by the compounds (II) and compound (III) through esterification reaction. The compounds (II) are cephalosporin antibiotics widely used in clinic, while the compound (III) can be synthesized according to the methods in 1984 <U.S. Pat. No. 4,444,686> (Vytautas J. Jasys etc) and <pharmaceutical industry, 1985, 16 (8), 346-9> (Jiang Naicai etc).

The compounds according to the invention can be synthesized by two distinct methods:

Method 1
(applicable to the synthesis of YR1-6)
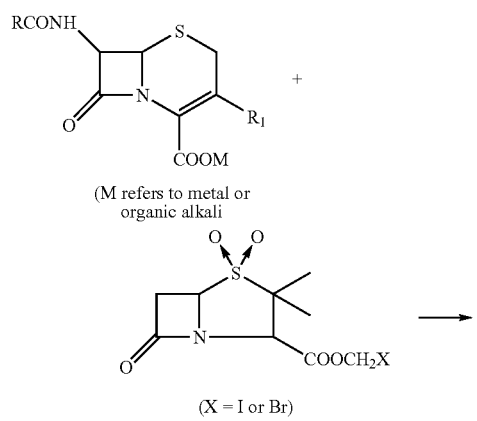
(M refers to metal or organic alkali)
(X = I or Br)
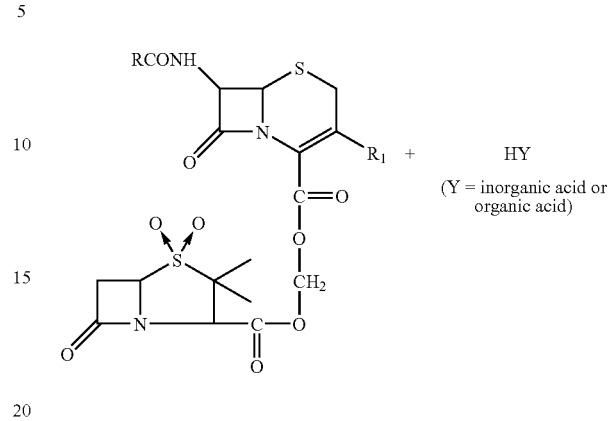
(Y = inorganic acid or organic acid)
Method 2
(applicable to the synthesis of YR3-6)
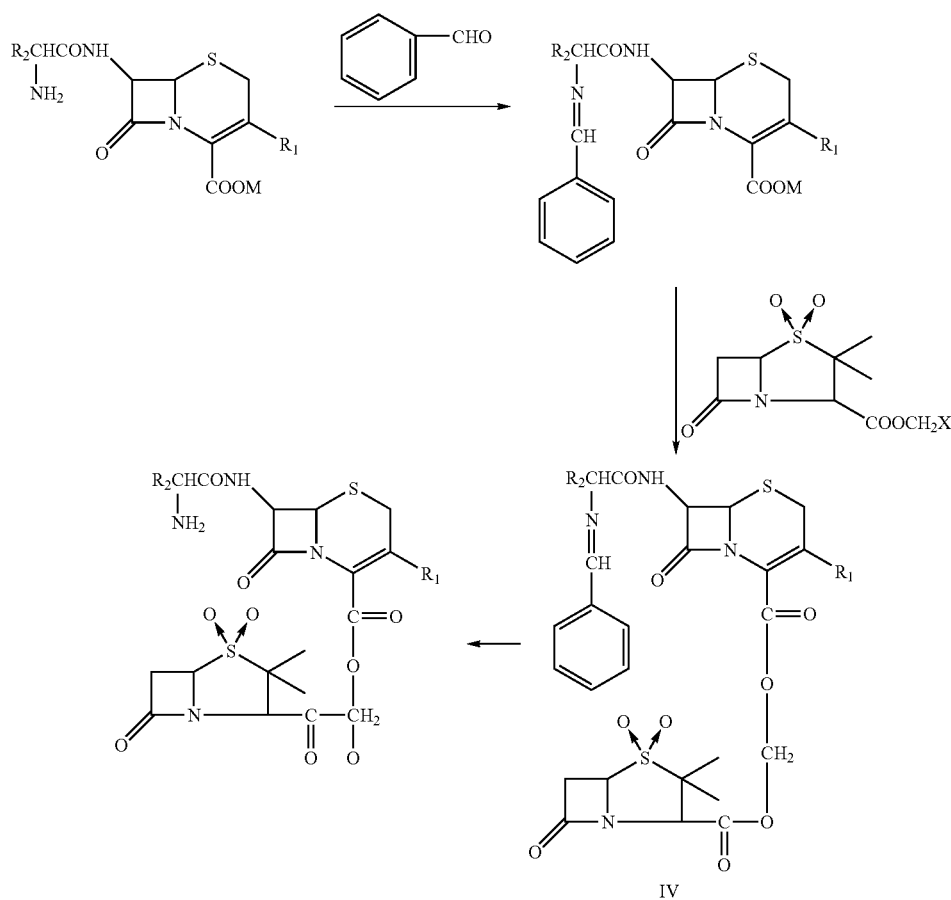
IV
$R_2 =$ ⌬ , ⌬ , HO-⌬
$R_1 = CH_3$, Method 1:

Salt of the compounds (II) such as sodium salt, potassium salt, magnesium salt, calcium salt, triethylamine salt, tributylamine salt, 1,8-diazacyclo [5,4,0] undecane-7-ene (DBU) salt, dicyclohexyl amine salt and tetrabutylammonium salt should be utilized when synthesizing the compounds (I) through method 1. The following examples introduce sodium salt, potassium salt, tributylamine salt and DBU salt of the compounds (II).

When synthesizing the compounds (I), the molar ratio of the compounds (II) and (III) can be from 1:0.9 to 1:1.5, and especially from 1:0.98 to 1:1. The reaction between the compounds (II) and (III) can occur at −15° C. to 30° C., and the reaction time generally varies from 30 minutes to 15 hours; adding 18 crownether-6, 16 crownether-4, 12 crownether-2, tetrabutyl ammonium hydrogen sulfate, tetrabutyl ammonium bromide during the process can promote the reaction.

Reaction solvent can be selected from the following substances: alkylogen such as dichloromethane, chloroform, dichloroethane etc; ketone such as acetone, cyclobutanone, cyclohexanone, methyl isobutyl ketone etc; polar aprotic solvent such as dimethyl acetamide, dimethylformamide, dimethyl sulfoxide etc. The following examples introduce the reaction method using dimethyl acetamide and dimethylformamide as solvent. The compounds and salts thereof according to the invention can be used to prepare oral antimicrobials, and the compounds according to the invention can be used to prepare a lot of inorganic salts and organic acid salts, such as hydrochloride, sulphate, p-toluenesulfonate, tartrate, maleate and lactate. The following examples introduce the preparation methods of p-toluenesulfonate and hydrochloride of the compounds according to the invention.

Method 2:

Method 2 is applicable to synthesize YR3-6, characterized in that the compounds (II) will react with benzaldehyde in the polar aprotic solvent such as dimethylformamide, dimethyl acetamide or in the low-grade alcohol such as methanol, alcohol, protecting α-amino on the lateral chain and forming Shiff bases, then synthesize intermediate compounds (IV) through method 1, and finally, react with Grignard reagent to remove protecting group to produce the compounds I (YR3-6) and salts thereof.

DETAILED DESCRIPTION OF THE INVENTION

Example 1

The potassium salt of compound (II-1) 11.0 g (0.025 mol) was suspended in 100 ml of dimethyl acetamide, stirred evenly, added 0.5 g of 18 crownether-6 to fully dissolve, then cooled the solution to 0° C., added 9.4 g (0.025 mol) of the compound (III) (X=I), stirred for 30 minutes at 0° C., and controlled the reaction using thin-layer chromatography*. When the material spot disappeared, added 200 ml of acetic ether and 200 ml of water into the reaction solution, stirred thoroughly and delaminated, separated out water layer, extracted using 200 ml of acetic ether, sequentially washed combined acetic ether layer with the mixture of 150 ml water plus 5 ml $NaHCO_3$ saturated aqueous solution and NaCl saturated aqueous solution, then decolored and dehydrated with activated carbon and magnesium sulfate anhydrous. Added 200 ml of isopropanol into oily substances acquired after decompressing and evaporating acetic ether, stirred at room temperature for 1 hour, white precipitate was separated out, then filtered and washed the filter cake with small quantity of isopropanol, dryed at room temperature in vacuo, got 12.9 g of white compound YR-1, 80% yield. High Pressure Liquid Chromatography showed that the purity was 98.5%.

* Silica gel plate HSGF254, developing agent isopropanol: ethyl acetate (2:1)

Compound (YR-1) Rf=0.8

The compound (I) was confirmed by IR and $^1$H NMR

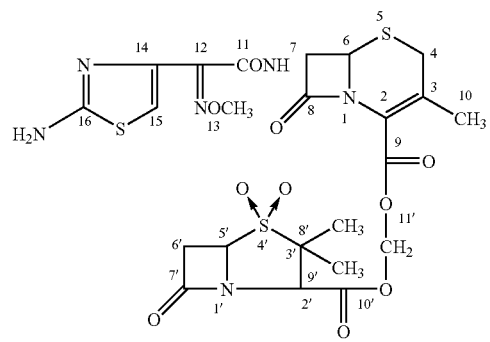

| IR (KBr disc) | | |
|---|---|---|
| absorption peak (cm$^{-1}$) | intensity | group |
| 3454.53 | Broad s | —$NH_2$ |
| 1784.53 | Broad s | β-lactam |
| 1734.4 | Broad s | —COOR |
| 1677.3 | s | —CONH— |
| 1623.31 | s | —C=C— |
| 1536.83 | s | —C=N— |
| 1320.76, 1120.38 | s | —C—O—C— |

| $^1$H NMR(DMSO d$_6$) | |
|---|---|
| chemical shift | genre |
| 9.6004(d, 1H, J = 8.4 H$_z$) | —CONH |
| 7.2335(broad s, 2H) | —$NH_2$ |
| 6.7512(s, 1H) | $C_{15}$—H |
| 5.9545(Abq, 2H, J = 6 H$_z$) | $C_{11'}$—H |
| 5.7445(dd, 1H, J = 5 H$_z$, 8 H$_z$) | $C_7$—H |
| 5.1903(m, 1H) | $C_{5'}$—H |
| 5.1518(d, 1H, J = 5 H$_z$) | $C_6$—H |
| 4.5297(s, 1H) | $C_{2'}$—H |
| 3.8352(s, 3H) | $C_{13}$—H |
| 3.6755(m, 2H) | $C_{6'}$—H |
| 3.6238, 3.4619(ABq, 2H, J = 18.5 H$_z$) | $C_4$—H |
| 2.1007(s, 3H) | $C_{10}$—H |
| 1.4820(s, 3H) | $C_{8'}$ or $C_{9'}$—H |
| 1.3765(s, 3H) | $C_{8'}$ or $C_{9'}$—H |

Example 2

Dissolved 4.6 g (0.03 mol) of DBU in 200 ml of dimethylformamide, stirred and cooled to 0° C., added 13.1 g (0.03 mol) of the compound (II-1) and 11.2 g (0.03 mol) of the compound (III) (X=I), reacted at below 0° C. for 30 minutes, trailed the reaction by thin-layer chromatography until the material spot disappeared. After the reaction finished, handled the reaction solution with the same method mentioned in example 1 and got 15.4 g of the compound YR-1, 80% yield. High Pressure Liquid Chromatography showed that the purity was 98.2%. The analytic results of IR and $^1$H NMR of the product was identical with those of example 1.

Example 3

The potassium salt of compound (II-1) 11.0 g (0.025 mol) was suspended in 150 ml of dimethyl acetamide, stirred and controlled at 20° C.~25° C., added 2.1 g (0.006 mol) of tetrabutyl ammonium hydrogen sulfate and 9.4 g (0.025 mol) of the compound (III) (X=I), reacted at the same temperature for 4-6 hours, and trailed the reaction by thin-layer chromatography until the material spot disappeared. After the reaction finished, handled the reaction solution with the same method mentioned in example 1 and got 13.7 g of the compound YR-1, 85% yield. High Pressure Liquid Chromatography showed that the purity was 98.7%. The analytic results of IR and $^1$H NMR of the product were identical with those of example 1.

Example 4

Stirred 6.45 g (0.01 mol) of the compound (YR-1) (got from example 2) at room temperature, dissolved in 65 ml of acetic ether, added 2.1 g (0.012 mol) of p-toluenesulfonic acid and stirred until solids were separate out, continued stirring for another 3 hours, filtrated, washed the solids with small quantity of acetic ether, dried in vacuo and got 7.2 g white p-toluenesulfonate of the compound (YR-1), 88% yield. High Pressure Liquid Chromatography showed that the purity was 98.5%.

P-toluenesulfonate of the compound (YR-1) was confirmed by IR and $^1$H NMR

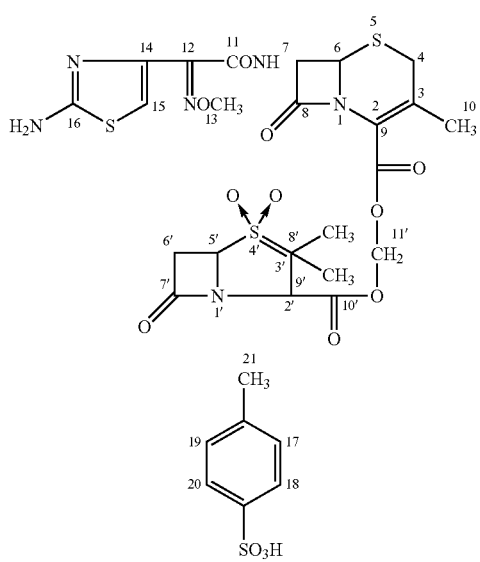

| $^1$H NMR (DMSO $d_6$) | |
|---|---|
| chemical shift | genre |
| 7.7107(d, 2H, J = 8 Hz) | $C_{18}$—H   $C_{20}$—H |
| 7.2326(d, 2H, J = 8 Hz) | $C_{17}$—H   $C_{19}$—H |
| 7.1304(s, 1H) | $C_{15}$—H |
| 5.9820(s, 1H) | $C_{11'}$—H |
| 5.7992(d, 1H, J = 5 Hz) | $C_7$—H |
| 5.1806(d, 1H, J = 5 Hz) | $C_6$—H |
| 4.9075(m, 1H) | $C_{5'}$—H |
| 4.4946(s, 1H) | $C_{2'}$—H |
| 4.0783(s, 3H) | $C_{13}$—H |
| 3.9187(m, 1H) | $C_{6'}$—H |
| 3.5824(m, 1H) | $C_{6'}$—H |
| 3.6568, 3.4267(ABq, 2H, J = 18 Hz) | $C_4$—H |
| 2.3703(s, 3H) | $C_{21}$—H |
| 2.1841(s, 3H) | $C_{10}$—H |
| 1.5688(s, 3H) | $C_{8'}$ or $C_{9'}$—H |
| 1.4591(s, 3H) | $C_{4'}$ or $C_{9'}$—H |

Example 5

The sodium salt of compound (II-2) 9.1 g (0.025 mol) was suspended in 100 ml of dimethyl acetamide, stirred and added 0.5 g of 18 crownether-6, cooled the mixture to −15° C., added 9.4 g (0.025 mol) of the compound (III) (X=I), and then stirred 3 hours. After the reaction finished, added 200 ml of acetic ether and 200 ml of water into the reaction solution, stirred thoroughly for 1 minutes and standed still to delaminate, seperated out acetic ether layer, and extracted water layer using 200 ml of acetic ether, combined organic phase, sequentially washed with 150 ml of diluted $NaHCO_3$ aqueous solution, 150 ml of water and 100 ml of saturated sodium chloride solution, and then decolored with activated carbon and dehydrated with magnesium sulfate anhydrous. Oily substances were acquired after decompressing and evaporating acetic ether, stirred these oily substances in 200 ml of isopropanol for 30 minutes, filtrated, washed with small quantity of isopropanol, dried and got 12.5 g of white solid of the compound YR-2, 85% yield. High Pressure Liquid Chromatography showed that the purity was 97.8%.

The compound YR-2 was confirmed by IR and $^1$H NMR

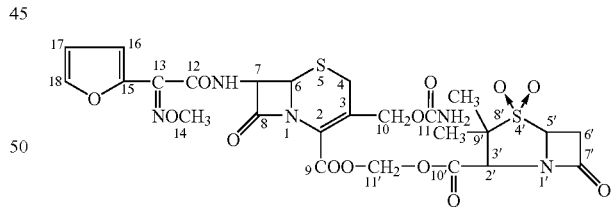

| IR (KBr disc) | | |
|---|---|---|
| absorption peak cm$^{-1}$ | intensity | group |
| 3456 | Broad s | —$NH_2$ |
| 1784.96 | Broad s | β-lactam |
| 1675.89 | s | 1675.89 |
| 1638.61 | s | —C=C— |
| 1541.32 | s | —C=N— |
| 1321.64, 1121.9 | s | —C—O—C— |

| IR (KBr disc) | | |
|---|---|---|
| absorption peak cm$^{-1}$ | intensity | group |
| 3485.34, 3376.65 | Broad m | —C(=O)—$NH_2$ |
| 1790.33 | Broad s | β-lactam |
| 1737.4 | s | —COOR |
| 1683.66 | s | —CONH— |
| 1599.48 | m | —C=C— |

| IR (KBr disc) | | |
|---|---|---|
| absorption peak cm$^{-1}$ | intensity | group |
| 1537.01 | m | —C=N— |
| 1324.65, 1120.67 | s | —C—O—C— |

| $^1$H NMR (DMSO d$_6$) | |
|---|---|
| chemical shift | genre |
| 9.8037 (d, 1H, J = 8 Hz) | CONH |
| 7.8390 (broad s, 1H) | C$_{18}$—H |
| 6.6938 (d, 1H, J = 3 Hz) | C$_{16}$—H |
| 6.6364 (broad s, 1H) | C$_{17}$—H |
| 6.5-6.8 (broad s, 2H) | $\overset{O}{\underset{\parallel}{-OC-NH_2}}$ |
| 6.0299, 5.9129 (ABq, 2H, J = 6 Hz) | C$_{11'}$—H |
| 5.8576 (dd, 1H, J = 5 Hz, 8 Hz) | C$_7$—H |
| 5.2520 (1H, J = 5 Hz) | C$_6$—H |
| 5.1829 (m, 1H) | C$_{5'}$—H |
| 4.8770, 4.6316 (ABq, 2H, J = 13 Hz) | C$_{10}$—H |
| 4.5329 (s, 1H) | C$_{2'}$—H |
| 3.8912 (s, 3H) | C$_{14}$—H |
| 3.6821 (m, 2H) | C$_{6'}$—H |
| 3.5571, 3.2685 (ABq, 2H, J = 18 Hz) | C$_4$—H |
| 1.4874 (s, 3H) | C$_{8'}$ or C$_{9'}$ methyl H |
| 1.3843 (s, 3H) | C$_{8'}$ or C$_{9'}$ methyl H |

Example 6

Added 5.6 g (0.03 mol) of tributylamine into 200 ml of dimethyl acetamide, stirred evenly and added 8.6 g (0.025 mol) of the compound (II-2), controlled at 20° C. and stirred to dissolve thoroughly, cooled to −15° C., added 9.4 g (0.025 mol) of the compound (III) (X=I), and stirred at −15° C. for 2 hours. Then, manipulated the rest steps according to the protocols used in example 5, and got 12.1 g of YR-2, 82% yield. High Pressure Liquid Chromatography showed that the purity was 98.2%. The analytic results of IR and $^1$H NMR of the product were identical with those of example 5.

Example 7

Added 3.6 g (0.01 mol) of the compound (II-3) into 36.5 ml of dimethyl acetamide, stirred and cooled to −10° C., added dropwisely 1.53 g (0.01 mol) of DBU to form solution, added 3.25 (0.01 mol) of the compound (III) (X=Br), stirred and reacted for 12 hours, added 100 ml of acetic ether, 30 ml of 3% NaHCO$_3$ solution and 50 ml of 15% NaCl aqueous solution into the reaction solution, stirred for 10 minutes and standed still, separated out organic layer, washed with 50 ml of 15% NaCl aqueous solution twice, decolored with activated carbon and dehydrated with magnesium sulfate anhydrous. Cooled to 0° C. and influxed with dry HCl gas to adjust pH to 2.5. At this moment, lots of solids were separated out, filtrated and washed with acetic ether three times, dried in vacuo and got 1.05 g of hydrochloride of the compound YR-3. High Pressure Liquid Chromatography showed that the purity was 97%.

The hydrochloride of the compound YR-3 was confirmed by IR and $^1$H NMR.

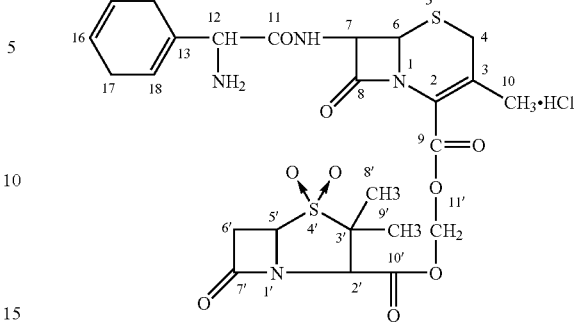

| IR (KBr disc) | | |
|---|---|---|
| absorption peak (cm$^{-1}$) | intensity | group |
| 3450, 3250, 2900 | Broad m | —NH$_2$, —NH |
| 1784.3 | Broad s | β-lactam and ester overlap |
| 1697.12 | m | —CONH— |
| 1321.81, 1156.16 | s | —C—O—C— |

| $^1$H NMR (DMSOd6) | |
|---|---|
| chemical shift | genre |
| 9.4450(d, 1H, J = 8 Hz) | —CONH |
| 8.4907(broad s, 3H) | —NH$_3^+$ |
| 6.0133, 5.9093(ABq, 2H, J = 6 Hz) | C$_{11'}$—H |
| 5.9599(broad s, 1H) | C$_{14}$—H |
| 5.7245(dd, 1H, J = 8 Hz) | C$_7$—H |
| 5.6799(m, 2H) | C$_{16}$—H, C$_{17}$—H |
| 5.1979(dd, 1H, J = 4.6 Hz, 1.6 Hz) | C$_{5'}$—H |
| 5.1418(d, 1H, J = 4.6 Hz) | C$_6$—H |
| 4.5294(s, 1H) | C$_{2'}$—H |
| 4.3972(broad s, 1H) | C$_{12}$—H |
| 3.7418, 3.6256(m, 2H) | C$_{6'}$—H |
| 3.4201, 3.3014(ABq, 2H, J = 16 Hz) | C$_4$—H |
| 2.7197, 2.5033(m, 4H) | C$_{15}$—H, C$_{18}$—H |
| 2.0550(s, 3H) | C$_{10}$—H |
| 1.4807(s, 3H) | C$_{8'}$—H or C$_{9'}$—H |
| 1.3738(s, 3H) | C$_{8'}$—H or C$_{9'}$—H |

Example 8

Added 3.6 g (0.01 mol) of the compound (II-3) into 36.5 ml of dimethyl acetamide, stirred and cooled to −10° C., added dropwisely 1.53 g (0.01 mol) of DBU to form clarifying solution, added 3.36 (0.009 mol) of the compound (III) (X=I), stirred and reacted for 12 hours, added 100 ml of acetic ether and 150 ml of pH1 HCl solution, stirred and delaminated, added 100 ml of acetic ether into water layer, adjusted pH to 7.5 using saturated NaHCO$_3$ solution, delaminated, washed organic layer with 50 ml mixture of 3% NaHCO$_3$ and 15% NaCl three times, decolored organic layer with activated carbon and dehydrated with magnesium sulfate anhydrous. Filtrated, cooled to 0° C. and influxed with dry HCl gas to adjust pH to 2.5. At this moment, lots of solids were separated out, filtrated, and washed the solids with acetic ether three times, dried in vacuo and got 0.9 g of hydrochloride of the compound YR-3. High Pressure Liquid Chromatography showed that the purity was 94.5%. The analytic results of IR and $^1$H NMR of the product were identical with those of example 7.

Example 9

Added 3.6 g (0.01 mol) of the compound (II-3) into 36.5 ml of dimethyl acetamide, stirred and cooled to −10° C., added dropwisely 1.53 g (0.01 mol) of DBU to form clarifying solution, added 5.6 g (0.015 mol) of the compound (III) (X=I), stirred and reacted for 12 hours, added 100 ml of acetic ether and 150 ml of pH1 HCl solution, stirred and delaminated, added 100 ml of acetic ether into water layer, adjusted pH to 7.5 using saturated NaHCO$_3$ solution, delaminated, washed organic layer with 50 ml mixture of 3% NaHCO$_3$ solution and 15% NaCl three times, decolored organic layer with activated carbon and dehydrated with magnesium sulfate anhydrous. Filtrated, cooled to 0° C., and influxed with dry HCl gas to adjust pH to 2.5. At this moment, lots of solids were separated out, washed the solids with acetic ether three times, dried in vacuo and got 0.95 g of hydrochloride of the compound YR-3. High Pressure Liquid Chromatography showed that the purity was 95.5%. The analytic results of IR and $^1$H NMR of the product were identical with those of example 7.

Example 10

Manipulated according to example 7, substituted DBU with 0.01 mol of dicyclohexyl amine, substituted bromomethyl ester with 0.01 mol of the compound (III) (X=I), the reaction time was 1.5 hours, got 1.15 g of hydrochloride of YR-3. High Pressure Liquid Chromatography showed that the purity was 96%. The analytic results of IR and $^1$H NMR of the product were identical with those of example 7.

Example 11

Added 3.72 g (0.01 mol) of sodium salt of the compound (1'-3) into 40 ml of dimethyl acetamide, stirred and cooled to 0° C., added 1.062 g (0.01 mol) of benzaldehyde and reacted for 10 hours at 0° C., cooled the reaction solution to −20° C., added 3.73 g (0.01 mol) of the compound (III) (X=I), stirred and reacted for 3 hours, added 110 ml of dichloromethane, 50 ml of 3% NaHCO$_3$ solution and 50 ml of 15% NaCl aqueous solution, stirred for 10 minutes and standed still to delaminate, seperated out organic phase, washed with 100 ml of pH7.5 phosphate buffer twice and with 100 ml of saturated NaCl aqueous solution twice, decolored organic phase with activated carbon and dehydrated with magnesium sulfate anhydrous. Concentrated in vacuo and got oily substances, then added 50 ml of ether and stirred to form 6.12 g white crystal of the compound IV

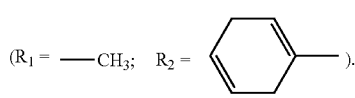

Dissolved 2.1 g of p-toluenesulfonic acid and 2.1 g of Grirnard reagent in 10 ml of methanol, added 4.78 g (0.01 mol) of the above product into this solution at room temperature, stirred for 30 minutes, decompressed and evaporated methanol, added 30 ml of dichloromethane and 30 ml of pH 7.5 phosphate buffer into the residues, stirred for 10 minutes and standed still to delaminate, separated water layer, steamed with 25 ml of dichloromethane three times. Washed the combined organic layer with saturated NaCl aqueous solution twice, removed the water layer, dried the organic phase with sodium sulphate anhydrous, cooled to 0° C. and influxed with dry HCl gas to adjust pH to 2.0, filtrated and collected solids, washed with small quantity of dichloromethane three times, dried in vacuo and got 3.8 g of hydrochloride of YR-3. High Pressure Liquid Chromatography showed that the purity was 96.5%. The analytic results of IR and $^1$H NMR of the product were identical with those of example 7.

Example 12

Added 3.65 g (0.01 mol) of the compound (1'-4) into 42 ml of dimethyl acetamide, stirred and cooled to −15° C., added dropwisely 1.53 g (0.01 mol) of DBU, stirred for 30 minutes, added 3.25 g (0.01 mol) of the compound (III) (X=Br) at the same temperature, stirred and reacted for 13 hours, added 100 ml of dichloromethane and 100 ml of pH7.5 phosphate buffer, stirred for 10 minutes and standed still to delaminate, sequentially washed the organic phase with 50 ml of pH7.5 phosphate buffer twice and saturated NaCl aqueous solution twice, then decolored with activated carbon, and dehydrated with magnesium sulfate anhydrous. Cooled to 0° C. and influxed with dry HCl gas to adjust pH to 2.0, filtrated and collected solids, washed with dichloromethane three times, dried in vacuo and got 1.8 g of hydrochloride of YR-4. High Pressure Liquid Chromatography showed that the purity was 97.2%.

The structure of hydrochloride of the compound YR-4 was confirmed by IR and $^1$H NMR.

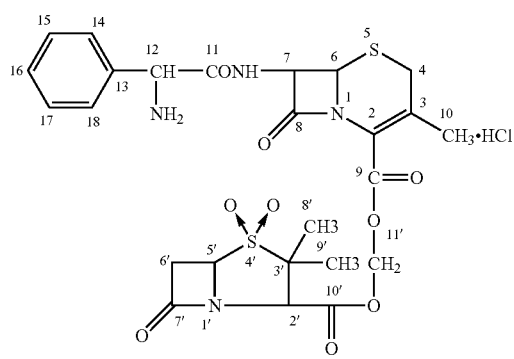

| IR (KBr disc) | | |
|---|---|---|
| absorption peak (cm$^{-1}$) | intensity | group |
| 3450, 3250, 2930.55 | Broad m | —NH$_2$, —NH |
| 1784.63 | Broad s | β-lactam and ester overlap |
| 1697.07 | m | —CONH— |
| 1321.36, 1156.95 | s | —C—O—C— |

| $^1$H NMR (DMSOd6) | |
|---|---|
| chemical shift | genre |
| 9.5752(d, 1H, J = 8 Hz) | —CONH— |
| 8.8117(s, 3H) | NH$_3^+$ |

-continued

| ¹H NMR (DMSOd6) | |
|---|---|
| chemical shift | genre |
| 7.5479-7.4162(m, 5H) | $C_{14,15,16,17,18}$—H |
| 6.0003, 5.8978(ABq, 2H, J = 6 Hz) | $C_{11'}$—H |
| 5.7593(dd, 1H, J = 8 Hz) | $C_7$—H |
| 5.1956(dd, 1H, J = 4.5 Hz, 1.5 Hz) | $C_{5'}$—H |
| 5.0472(s, 1H) | $C_{12}$—H |
| 5.0394(d, 1H, J = 4.7 Hz) | $C_6$—H |
| 4.5245(s, 1H) | $C_{2'}$—H |
| 3.7049(dd, 1H, J = 15 Hz, 4.5 Hz) | $C_{6'}$—H |
| 3.3689(dd, 1H, J = 15 Hz, 1.5 Hz) | $C_{6'}$—H |
| 3.5419, 3.2743(ABq, 2H, J = 18 Hz) | $C_4$—H |
| 2.0154(s, 3H) | $C_{10}$—H |
| 1.4477(s, 3H) | $C_{8'}$ or $C_{9'}$—H |
| 1.3674(s, 3H) | $C_{8'}$ or $C_{9'}$—H |

Example 13

Added 4.03 g (0.01 mol) of potassium salt of the compound (II-4) into 50 ml of dimethyl acetamide, stirred and cooled to 0° C., added 1.062 g (0.01 mol) of benzaldehyde and reacted for 8 hours at 0° C.-5° C., cooled the reaction solution to −15° C., added 3.73 g (0.01 mol) of the compound (III) (X=I), stirred and reacted for 2 hours. The other reaction steps were performed according to example 9, got 6.05 g of white crystal of intermediate product-compound (IV)

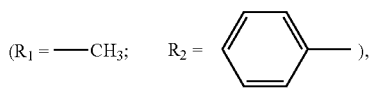

and finally got 3.65 g of hydrochloride of YR-4. The analytic results of IR and ¹H NMR of the product were identical with those of example 10.

Example 14

3.65 g (0.01 mol) of the compound (II-5) was suspended in 37 ml of dimethylformamide, cooled it to −20° C., added 1.51 g (0.01 mol) of DBU and stirred to dissolve, added 3.73 (0.01 mol) of the compound (III) (X=I), stirred for 30 minutes, added 37 ml of acetic ether and 80 ml of aqueous solution consisting of 15% NaCl and 5% NaHCO₃, stirred for 10 minutes and delaminated, separated organic layer and washed with the above aqueous solution consisting of 15% NaCl and 5% NaHCO₃ twice, dehydrated with magnesium sulfate anhydrous, filtrated and influxed with dry HCl gas to adjust pH to 2-3. After crystal was separated out, continued stirring for 10 minutes, filtrated and washed with small quantity of acetic ether, dried in vacuo and got 3.7 g white crystal of hydrochloride of the compound YR-5. High Pressure Liquid Chromatography showed that the purity was 95.6%.

The hydrochloride of the compound YR-5 was confirmed by IR and ¹H NMR.

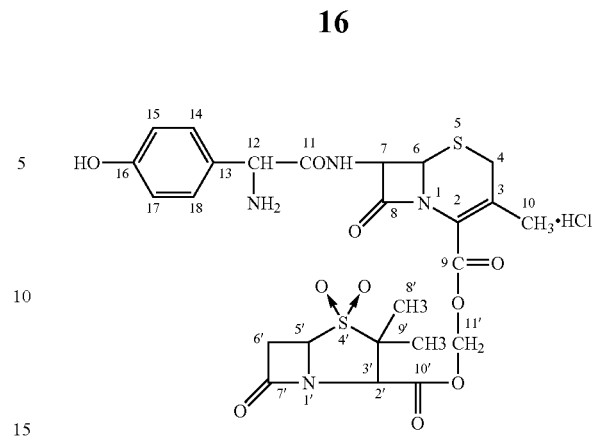

| IR (KBr disc) | | |
|---|---|---|
| absorption peak (cm⁻¹) | intensity | group |
| 3400, 3200, 2900 | Broad m | —NH₂, —NH, —OH |
| 1779.61 | Broad s | β-lactam and ester overlap |
| 1693.71 | m | —CONH— |
| 1320.64, 1183.04 | s | —C—O—C— |

| ¹H NMR (DMSOd6) | |
|---|---|
| chemical shift | genre |
| 9.1868(s, 1H) | —OH |
| 9.4460(d, 1H, J = 8 Hz) | —CONH— |
| 8.6479(s, 3H) | $NH_3^+$ |
| 7.2958(d, 2H, J = 8.5 Hz) | $C_{14}, C_{18}$—H |
| 6.7917(d, 2H, J = 8.5 Hz) | $C_{15}, C_{17}$—H |
| 5.9990, 5.8974(ABq, 2H, J = 6 Hz) | $C_{11'}$—H |
| 5.7392(dd, 1H, J = 8Hz, 4.5 Hz) | $C_7$—H |
| 5.1907(d, 1H, J = 4.0 Hz) | $C_{5'}$—H |
| 5.0478(d, 1H, J = 4.5 Hz) | $C_6$—H |
| 4.9200(broad s, 1H) | $C_{12}$—H |
| 4.5206(s, 1H) | $C_{2'}$—H |
| 3.6997(dd, 1H, J = 16.5 Hz, 4.0 Hz) | $C_{6'}$—H |
| 3.3881(dd, 1H, J = 16.5 Hz,) | $C_{6'}$—H |
| 3.5535, 3.2734(ABq, 2H, J = 18 Hz) | $C_4$—H |
| 2.0171(s, 3H) | $C_{10}$—H |
| 1.4759(s, 3H) | $C_{8'}$ or $C_{9'}$—H |
| 1.3674(s, 3H) | $C_{8'}$ or $C_{9'}$—H |

Example 15

Added 4.01 g (0.01 mol) of potassium salt of the compound (II-5) into 15 ml of dimethylformamide, cooled to 0° C., added 1.27 g (0.012 mol) of benzaldehyde and stirred and reacted for 8 hours, added 3.73 g (0.01 mol) of the compound (III) (X=I), stirred and reacted for 30 minutes, added 40 ml of acetic ether and 80 ml aqueous solution consisting of 15% NaCl and 5% NaHCO₃, stirred for 10 minutes and delaminated, separated out organic layer and washed with saturated NaCl aqueous solution, dehydrated with magnesium sulfate anhydrous, filtrated, decompressed and evaporated organic solvent, and then added 50 ml of isopropyl ether and stirred to form 6.1 g of yellow crystal of the compound (IV)

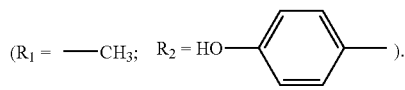

The other reaction steps were performed according to example 9, got 2.56 g of hydrochloride of YR-5. High Pressure Liquid Chromatography showed that the purity was 97.2%. The analytic results of IR and $^1$H NMR of the product were identical with those of example 12.

In order to further demonstrate the antibacterial effects of the compounds according to the invention and use thereof, YR-1 and YR-2 was chosen to perform in vitro antibacterial activity experiment, ex vivo antibacterial activity experiment after mouse is administered and mouse maximum tolerable dose experiment, all of which were accomplished by Shanghai Institute of Pharmaceutical Industry.

Effectiveness Example 1

In Vitro Antibacterial Activity Experiment

1. Experiment Materials:

tested samples YR-1, YR-2 were the ones prepared in example 1 and example 5 respectively, control samples were cefetamet sodium (CTM), cefuroxime sodium (CRX), cefetamet sodium+sulbactam sodium (CTM+SBT) (molar ratio 1:1), cefuroxime+sulbactam sodium (CRX+SBT) (molar ratio 1:1). All control samples (have been sold on the market) were supplied by Zhejiang Yongning pharmaceutical factory.

2. Experiment Bacteria Strains:

Staphylococcus aureus 26003, Diplococcus lanceolatus 31002, E. coli 44102, Shigella sonnet 51081, Shigella bogdii 51313, Shigella flexneri 51573, Proteus mirabilis 49005, Bacillus proteus 49085, Proteus morganii 49086, Pseudomonas aeruginosa 10124, Bacillus pneumoniae 46101, Salmonella enteritidis 50041, Salmonella typhi 50097, Citrobacter 48017, Candida ciferii 41002 were supplied by Shanghai Hygienic and Antiepidemic Station.

Staphylococcus epidermidis 26069 and Bacillus aerogenes 45102 were supplied by Beijing Drug & Biology Product Appraisal Bureau.

Diplococcus lanceolatus 0031 was supplied by Shanghai First People's Hospital.

3. Culture Medium:

Mueller-Hinton Agar (M.H) culture medium, batch number 20040528 (Shanghai Reagent Supply Research Center, China Diarrhea Disease Control).

4. Experiment Methods:

Adopted agar double dilution, inoculated using multipoint inoculator, inoculated $10^5$CFU/ML each point, cultured for 24 hours at 37° C., observed and recorded the results, set the least concentration of the antibacterial drug that can inhibit bacteria growth as the minimum inhibitory concentration (MIC).

5. Experiment Results:

| | MIC of the drug to bacteria (μg/ml) | | | | | |
|---|---|---|---|---|---|---|
| Bacteria strain | cefetamet (CTM) | cefuroxime (CRX) | Cefetamet + Sulbactam (CTM + SBT) | Cefuroxime + Sulbactam (CRX + SBT) | YR-1 | YR-2 |
| Staphylococcus aureus 26003 | 100 | 1.56 | 50 | 3.13 | 100 | 6.25 |
| Diplococcus lanceolatus 31002 | >100 | 25 | 50 | 25 | 100 | 25 |
| E. coli 44102 | 0.78 | 6.25 | 0.78 | 6.25 | 1.56 | 12.5 |
| Shigella sonnet 51081 | 0.39 | 0.78 | 0.195 | 1.56 | 0.39 | 1.56 |
| Shigella bogdii 51313 | 0.39 | 1.56 | 0.195 | 1.56 | 0.39 | 1.56 |
| Proteus mirabilis 49005 | 0.195 | 1.56 | 0.39 | 3.13 | 0.098 | 3.13 |
| Bacillus proteus 49085 | 0.195 | 0.78 | 0.39 | 1.56 | 0.195 | 0.78 |
| Proteus morganii 49086 | >100 | 100 | 3.13 | 12.5 | 0.78 | 25 |
| Pseudomonas aeruginosa 10124 | 100 | 100 | 100 | 100 | 100 | 100 |
| Bacillus pneumoniae 46101 | 0.78 | 25 | 0.78 | 12.5 | 0.78 | 12.5 |
| Salmonella enteritidis 50041 | 0.78 | 6.25 | 0.78 | 6.25 | 1.56 | 12.5 |
| Salmonella typhi 50097 | 0.78 | 3.13 | 0.78 | 3.13 | 1.56 | 6.25 |
| Citrobacter 48017 | 1.56 | 1.56 | 1.56 | 3.13 | 1.56 | 3.13 |
| Bacillus aerogenes 45102 | 0.195 | 3.13 | 0.39 | 6.25 | 0.39 | 6.25 |
| Candida ciferii 41002 | 0.78 | 25 | 0.78 | 25 | 0.78 | 50 |
| Shigella flexneri 51573 | 0.78 | 1.56 | 0.78 | 3.13 | 0.39 | 3.13 |
| Staphylococcus epidermidis 26069 | 12.5 | 0.39 | 25 | 0.78 | 50 | 0.78 |
| Diplococcus lanceolatus 0031 | 25 | 0.78 | 25 | 0.78 | 50 | 0.78 |

6. Conclusions:

Both YR-1 and YR-2 have antibacterial activity in vitro. Their antibacterial activities are nearly equal to CTM+SBT and CRX+SBT respectively. Both YR-1 and YR-2 have stronger antibacterial activities to β-lactamase releasing Gram negative bacteria than those of CTM or CRX used solely, for example, to *Proteus morganii* 49086, MICs of CTM and CRX are >100 mg/ml and 100 mg/ml respectively, while MICs of YR-1 and YR-2 are 0.78 mg/ml and 25 mg/ml respectively, the antibacterial activities enhanced one hundred times and four times respectively. CTM belongs to the third generation of cephalosporin, which has no effects to Gram positive bacteria and *Pseudomonas aeruginosa*, CRX belongs to the second generation of cephalosporin, which has weak effects to Gram positive bacteria and has no effects to *Pseudomonas aeruginosa*, and YR-1 and YR-2 show the same results. To some bacteria without enzyme releasing, YR-1 and YR-2 show the same antibacterial activities as CTM and CRX.

Effectiveness Example 2

Ex Vivo Antibacterial Activity Experiment After Mouse is Administered

1. Experiment Materials the sources of tested samples (YR-1, YR-2) and control samples (CTM, CRX, CTM+SBT 1:1 and CRX+SBT 1:1) are the same as above.

2. Experiment Bacteria Strains:

*Bacillus proteus* 49085, *Proteus morganii* 49086, inoculated $10^5$CFU/ML each dish.

3. Culture Medium:

Mueller-Hinton Agar (M.H) culture medium, batch number 000707 (Shanghai Reagent Supply Research Center, China Diarrhea Disease Control).

4. Experiment Animals:

Strain: Kunming mice; source: Animal Facility of Shanghai Institute of Pharmaceutical Industry; certificate number: Hudonghezhengzi No. 107; animal numbers: 120; Sex: same number of male and female mice; Body weight: 18-21 g; fast time: 16 hours.

5. Experiment Methods:

Group 1: CTM, CRX, CTM+SBT 1:1, CRX+SBT 1:1 were given at a dosage of 500 mg/kg intravenously, collecting blood at 10 minutes, 30 minutes, 1 hour, 2 hours, 4 hours, 8 hours after administration.

Group 2: YR-1, YR-2 were given at a dosage of 1000 mg/kg via intragastric administration, collecting blood at 10 minutes, 30 minutes, 1 hour, 2 hours, 4 hours, 8 hours after administration.

Kunming mice were randomly divided into several groups according to body weight of empty stomach and sex. Collecting blood of three mice at different time point, anticoagulated with heparin, centrifugated and separated plasma, quantitative spotting, semi-quantitated antibacterial activity according to the size of bacterial inhibition ring.

6. Experiment Results:

Results of ex vivo antibacterial activity to *Bacillus proteus* 49085

| | | Cefetamet sodium (CTM) | Cefuroxime sodium (CRX) | Cefetamet sodium + sulbactam (CTM + SBT) | cefuroxime + sulbactam (CRS + SBT) | YR-1 | YR-2 |
|---|---|---|---|---|---|---|---|
| No. | | 1 | 2 | 3 | 4 | 6 | 5 |
| administration manner | | intravenous injection | intravenous injection | intravenous injection | intravenous injection | intragastric administration | intragastric administration |
| Dosage | | 500 mg/kg | 500 mg/kg | 500 mg/kg | 500 mg/kg | 1000 mg/kg | 1000 mg/kg |
| collecting | 10 min | +++ | +++ | ++ | ++ | − | − |
| blood | 30 min | +++ | +++ | ++ | ++ | + | + |
| time | 1 hr | +++ | ++ | + | + | + | + |
| point and | 2 hr | ++ | + | + | + | + | + |
| antibacterial | 4 hr | ± | + | + | + | + | + |
| activity | 8 hr | − | − | − | − | + | ± |

Results of ex vivo antibacterial activity to *Proteus morganii* 49086

| | | Cefetamet Sodium (CTM) | Cefuroxime sodium (CRX) | Cefetamet sodium + sulbactam (CTM + SBT) | cefuroxime + sulbactam (CRS + SBT) | YR-1 | YR-2 |
|---|---|---|---|---|---|---|---|
| No. | | 1 | 2 | 3 | 4 | 6 | 5 |
| administration manner | | intravenous injection | intravenous injection | intravenous injection | intravenous injection | intragastric administration | intragastric administration |
| dosage | | 500 mg/kg | 500 mg/kg | 500 mg/kg | 500 mg/kg | 1000 mg/kg | 1000 mg/kg |
| collecting | 10 min | ++ | + | ++ | + | − | − |
| blood | 30 min | + | + | ++ | + | + | + |
| time | 1 hr | + | + | + | + | + | + |
| point and | 2 hr | + | + | + | + | + | + |
| antibacterial | 4 hr | ± | + | ± | ± | + | + |
| activity | 8 hr | − | − | − | − | + | + |

7. Conclusions:

Antibacterial activities can be detected in the blood of mice orally adminstered with YR-1 and YR-2. Mice show stable and persistent blood drug concentrations after given YR-1 and YR-2 via intragastric administration. Antibacterial activities of YR-1 and YR-2 can be detected even 8 hours after administration, while considering that CTM, CRX, CTM+SBT and CRX+SBT can not be absorbed via oral administration, they all are given via intravenous injection, and they are easy to reach blood peak concentration and show stronger antibacterial activities, but their metabolism is much more quicker. Antibacterial activities of CTM, CRX, CTM SBT and CRX+SBT can not be detected 8 hours after administration. It demonstrates that YR-1 and YR-2 have longer half-life period and prolonged effects.

Toxic reaction: recorded behaviors of mice, skin, respiration, urination and defecation, appetite, checked if there are abnormal secretions appeared in the nose, eye and mouth.

Observation period: 7 days, killed all the surviving mice after observation period, and autopsied to see if there is any abnormality existed in the mice organs.

7. Experiment Results:

After fasted for 16 hours and given YR-1 or YR-2, mice showed no obvious abnormal symptoms of toxic reactions, mice activities had no obvious changes, and no abnormalities were observed in the organs after killed.

| | | | | Acute toxicity test of YR-1 and YR-2 on mice | | | | | | | |
|---|---|---|---|---|---|---|---|---|---|---|---|
| | | | | | Death number during observation | | | | | | |
| | | Dosage | Mice | | | | | | | | |
| sample | group | (g/kg/24 hr) | number | 1 | 2 | 3 | 4 | 5 | 6 | 7 (day) | Death rate % |
| YR-1 | female | 5 | 10 | 0 | 0 | 0 | 0 | 0 | 0 | 0 | 0 |
| | male | 5 | 10 | 0 | 0 | 0 | 0 | 0 | 0 | 0 | 0 |
| YR-2 | female | 5 | 10 | 0 | 0 | 0 | 0 | 0 | 0 | 0 | 0 |
| | male | 5 | 10 | 0 | 0 | 0 | 0 | 0 | 0 | 0 | 0 |

Effectiveness Example 3

Mouse Maximum Tolerable Dose Experiment

1. Experiment Materials:

tested samples (YR-1, YR-2) are the same as above.

2. Experimental Animals:

Strain: Kunming mice; source: Animal Facility of Shanghai Institute of Pharmaceutical Industry; certificate number: Hudonghezhengzi No. 107; animal numbers: 20; Sex: same number of male and female mice; Body weight: 18-21 g; fast time: 16 hours.

3. Dosage:

Preparation of samples: 5 g/kg (prepared with 5% carboxymethyl cellulose CMC); volume accepted: 0.6 ml/20 g body weight/each time; administration times: once; dosage: 5 g/kg/24 hr 4. Administration Manner:

Intragastric Administration

5. Experiment Methods:

20 mice, 10 male and 10 female, were given YR-1 or YR-2 via intragastric administration, observed manifestation of mice toxic symptom immediately after administration, recorded mice death number.

6. Observing Index:

Observed manifestation of mice toxic symptom immediately after administration, observed twice each day (morning and evening).

Death: recorded dead mice immediately and observed changes of main organs of mice including heart, liver, spleen, lung, kidney etc with naked eyes; if abnormality was observed with naked eyes, performing pathologic examination.

8. Conclusions:

Due to low toxicity of YR-1 and YR-2, there was no way to determine $LD_{50}$, maximum tolerable dose test was performed, we can learn from the results that $LD_{50}>5$ g/kg. This demonstrates that YR-1 and YR-2 are kinds of safe and low toxical drugs that could be taken orally.

What is claimed is:

1. An intermediate compound represented by formula (IV) as follows:

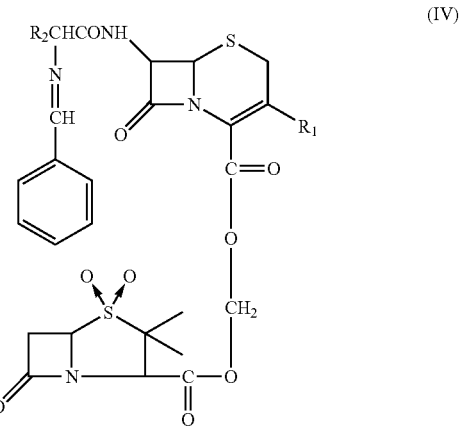

wherein,
$R_1 = CH_3$ or Cl;

$R_2 = $ [phenyl] or [phenyl] or [phenyl]—OH.

* * * * *